United States Patent
Ozero (10) Patent No.: US 11,608,305 B2
(45) Date of Patent: Mar. 21, 2023

(54) ETHYLENE OXIDE PURIFICATION

(71) Applicants: Petron Scientech, Inc., Princeton, NJ (US); Scientech Associates Inc., Westhampton Beach, NY (US)

(72) Inventor: Brian J. Ozero, Westhampton Beach, NY (US)

(73) Assignees: Petron Scientech, Inc., Princeton, NJ (US); Scientech Associates Inc., Westhampton Beach, NY (US)

(*) Notice: Subject to any disclaimer, the term of this patent is extended or adjusted under 35 U.S.C. 154(b) by 0 days.

(21) Appl. No.: 17/760,680

(22) PCT Filed: Sep. 3, 2020

(86) PCT No.: PCT/US2020/049136
§ 371 (c)(1),
(2) Date: Mar. 15, 2022

(87) PCT Pub. No.: WO2021/055174
PCT Pub. Date: Mar. 25, 2021

(65) Prior Publication Data
US 2022/0348528 A1 Nov. 3, 2022

Related U.S. Application Data

(60) Provisional application No. 62/900,952, filed on Sep. 16, 2019.

(51) Int. Cl.
*C07D 301/32* (2006.01)
*C07C 29/80* (2006.01)
(Continued)

(52) U.S. Cl.
CPC .............. *C07C 29/80* (2013.01); *C07C 29/38* (2013.01); *C07D 301/32* (2013.01); *C07D 303/04* (2013.01)

(58) Field of Classification Search
CPC ....... C07C 29/80; C07C 29/38; C07C 29/106; C07C 31/20; C07C 29/10; C07C 29/76; C07D 301/32; C07D 303/04
(Continued)

(56) References Cited

U.S. PATENT DOCUMENTS

| 4,134,797 A | 1/1979 | Ozero |
| 7,569,710 B1 | 8/2009 | Ozero |

FOREIGN PATENT DOCUMENTS

WO  2019101707 A1  5/2019

OTHER PUBLICATIONS

International Search Report and Written Opinion for International Application No. PCT/US2020/049136, dated Dec. 2, 2020, 9 pages.
(Continued)

*Primary Examiner* — Taylor V Oh
(74) *Attorney, Agent, or Firm* — RatnerPrestia (57) ABSTRACT

An improved process for the recovery of high-purity ethylene-oxide water feed streams to EO purification and MEG reaction units when both are operating in EO plants that incorporate EO Stripper bypass technology, by installing a second lights stripper to exclusively degasify the diluted EO feed to the MEG reactor, thus permitting the use of additional bypassed (gasified) EO absorbate as the diluent and resulting in a substantial increase in the total amount of EO absorbate that can bypass the EO Stripper.

9 Claims, 4 Drawing Sheets

(51) Int. Cl.
   *C07C 29/38* (2006.01)
   *C07D 303/04* (2006.01)
(58) Field of Classification Search
   USPC .................................................. 549/541, 538
   See application file for complete search history.

(56) References Cited

OTHER PUBLICATIONS

International Preliminary Report on Patentability and Written Opinion for International Application No. PCT/US2020/049136, dated Mar. 15, 2022, 8 pages.

ETHYLENE OXIDE PURIFICATION

CROSS-REFERENCE TO RELATED APPLICATIONS

This is the U.S. National Phase application of PCT/US2020/49136, filed 3 Sep. 2020, which claims priority to U.S. Provisional Patent Application No. 62/900,952, filed 16 Sep. 2019, entitled "ETHYLENE OXIDE PURIFICATION" the contents of each of which are incorporated herein by reference in their entireties.

FIELD OF THE INVENTION

This invention relates to a method of improving the purity of the ethylene oxide (EO) recovered from the gaseous effluent from an ethylene oxide reactor of a combined ethylene oxide/ethylene glycol plant when the purified gaseous effluent is recovered as aqueous ethylene oxide solutions and used as feeds to both ethylene oxide purification columns and to ethylene glycol units that are integrated into the combined ethylene oxide/ethylene glycol plant. The method relates to improving both the ethylene oxide stripping system and the ethylene oxide reabsorption system to reduce operating costs and provide simplifications to the overall operation of the combined ethylene oxide/ethylene glycol plant. Such ethylene oxide stripping and ethylene oxide reabsorption systems are commonly used in the EO recovery step to produce two pure ethylene oxide-water feed streams with differing EO concentrations. One stream is used as feed to a column or series of columns that further purify the EO to produce high purity EO and the other, lower concentration stream is used as the feed to an ethylene glycol plant that produces polyester fiber grade ethylene glycol.

BACKGROUND OF THE INVENTION

When ethylene oxide (EO) is produced by silver-catalyzed, vapor-phase partial oxidation of ethylene by molecular oxygen, the EO product is in a hot gaseous effluent stream from the reactor. The ethylene oxide content in this reactor effluent is quite low and therefore requires recovery, further purification and must be concentrated as well. This recovery of the ethylene oxide from the reactor effluent gas, as conventionally practiced, involves cooling of the reaction effluent gases in a heat exchanger train and absorption in water. The water absorption step produces a very dilute EO solution together with various impurities. Ethylene oxide is then stripped from this dilute solution and the EO gas thus stripped is then reabsorbed in recycled EO-free process water to produce the more concentrated EO solutions required to be fed to the columns producing the high purity EO and also to be fed to the plant that produces fiber-grade ethylene glycol.

As described in U.S. Pat. No. 7,569,710, the entire contents of which are incorporated by reference herein for all purposes, the cooled EO reactor effluent gas is sent to an EO absorber, which may contain a quench section in the lower part of the absorber column where the reactor effluent is scrubbed with a recirculated, cooled aqueous alkaline stream to absorb and neutralize acidic compounds such as acetic and formic acids and also to absorb almost all of the trace amount of by-product formaldehyde (which is present as methylene glycol) prior to moving through the upper section of the EO absorber column. Also as disclosed in U.S. Pat. No. 7,569,710, the reactor effluent may be passed through a separate quench column where the same scrub with an alkaline stream is performed, before being passed to the absorber.

A liquid bleed stream is removed from the quench (also called a scrubber or a quench scrubber) step. This is done whether a separate alkaline quench column is used or if the alkaline quench scrubbing step is performed in the bottom of the absorber column. The purpose of this bleed is to remove the extra water that would otherwise accumulate in the recirculation loop. This water is formed as a by-product during the oxidation of ethylene to ethylene oxide. This by-product water is almost all condensed during the quenching/scrubbing step.

Then, the treated vaporous reaction stream from the alkaline quench scrub step is passed through liquid de-entrainment devices and fed to a water wash step where it is washed with fresh process water to remove any entrained quench liquid and to absorb any remaining formaldehyde vapor. After this washing step, the vaporous reaction stream is passed through liquid de-entrainment devices and then fed to the bottom of an ethylene oxide absorber column, where it is counter-currently washed with recirculated, EO-free process water to absorb the ethylene oxide and produce a high-purity EO-containing absorbate. The quench bleed, which in addition to the water mentioned above, contains typically 0.5-5 wt. % of EO and comparable concentrations of glycol and sodium salts as well as a low concentration of formaldehyde (as methylene glycol) is sent to a quench bleed stripper where the EO is stripped out and recovered. The EO-free quench stripper bottoms can then be disposed of as a waste stream or processed separately for recovery of the small quantity of crude ethylene glycol that it contains.

In EO reaction systems that include an EO stripper bypass stream flow scheme (as described in U.S. Pat. No. 7,569,710), the EO absorbate (i.e. a water/ethylene oxide solution) from the EO absorber is pure enough to be fed directly to the purification column(s) that produce high purity ethylene oxide (HPEO) and/or reactors that produce ethylene glycol. However, while the purity of this aqueous solution is acceptable, the concentration of EO in the water is normally too low for either of these process routes to be economically feasible. Accordingly, in these plants, only part of the dilute EO absorbate is sent directly to the EO reabsorber, bypassing the main EO stripper. The balance of the EO absorbate is fed to the EO Stripper to produce concentrated EO vapor that, when reabsorbed in the bypassed EO absorbate, will raise its EO concentration to the higher levels required in the feed to an EO purification system and/or a glycol reactor.

The concentrated EO bottoms from the EO reabsorber, which contain small concentrations of absorbed $CO_2$ and reaction gases, are then normally fed to a single lights stripper in which low pressure steam is injected to strip out the $CO_2$ and other light components before being pumped to the high purity ethylene oxide (HPEO) purification column and/or the reactor that produces ethylene glycol, also referred to as monoethylene glycol (MEG).

The most suitable EO concentration in the feed to a large, single high purity ethylene oxide (HPEO) purification column, such as described in U.S. Pat. No. 4,134,797, the entire contents of which are incorporated by reference herein for all purposes, is normally in the range of 10-13 wt. % in water, whereas the normal EO concentration range in the feed to an MEG reactor would be in the range 6-10 wt. % EO in water. The higher water to EO ratio is desirable in order to limit the production of heavier glycols.

Accordingly, when both the column that produces high purity ethylene oxide and the reactor that produces fiber grade monoethylene glycol are operating at comparable ethylene oxide equivalent (EOE) capacities with similar net feed rates of ethylene oxide, but with the different required EO concentrations in their feed streams, the EO reabsorber would normally be operated to produce EO reabsorber bottoms feed to the single lights stripper with the higher EO concentration required by the HPEO Column. This is the controlling EO concentration that therefore sets and limits the amount of EO absorbate that can bypass the EO stripper in a plant that uses this process scheme. The desired more dilute EO feed to the MEG reactor is then produced by mixing part of the bottoms from the lights stripper with EO-free recycle process water.

However, even with the benefits of utilizing the EO process that incorporates the EO bypass flow scheme, there is still scope for process improvements in terms of energy efficiency and simplification of the process.

SUMMARY OF THE INVENTION

The present invention provides an improved method of purification of ethylene oxide which comprises quenching and washing the ethylene oxide reactor effluent by contact with a recirculated, cooled, aqueous alkaline stream and a water wash, passing the gaseous ethylene oxide containing stream obtained from the alkaline quenching wash to an ethylene oxide absorber. In the ethylene oxide absorber, the ethylene oxide is absorbed in once-through EO-free process water to form a dilute aqueous ethylene oxide-containing absorbate solution. Next, a portion of this ethylene oxide-containing dilute absorbate solution is stripped in an EO stripper to produce a gaseous ethylene oxide overhead vapor. The gaseous ethylene oxide overhead vapor is then passed to an ethylene oxide reabsorber where the ethylene oxide is absorbed in another portion of the dilute aqueous ethylene oxide-containing absorbate which bypassed the EO stripper. Thus, an EO aqueous reabsorbate solution having a higher content of EO than the ethylene oxide-containing dilute absorbate solution emerges from the EO reabsorber. A portion of this enriched-in-EO reabsorbate solution passes to a first lights stripper designed to remove dissolved carbon dioxide with a lights-free, concentrated ethylene oxide-containing solution being recovered for use as high-purity feed to only a high purity EO distillation system.

In a preferred embodiment, from 10-90%, more preferably 20-80%, and most typically 25-35% of the dilute ethylene oxide solution obtained from the absorber is passed directly to the reabsorber, and never passes through the EO stripper, thus reducing the stripping steam consumed in the EO Stripper by 25-35%.

Additionally, another portion of the reabsorber bottoms (i.e. the EO enriched absorbate) is mixed with additional bypassed dilute EO absorbate (that bypasses both the EO stripper and the EO reabsorber) and an acetaldehyde-EO purge from the high purity EO distillation system. This gasified mixture is fed to a second lights stripper that will then produce lights-free aqueous bottoms containing a lower EO concentration than the feed to the high purity EO distillation system. This lower EO concentration is the correct, lower concentration of EO/higher concentration of water that the MEG reactor requires to reduce the yield of heavier glycols. This entire process which also serves to dilute the EO stream fed to the glycol reactor also substantially increases the total quantity of dilute EO absorbate that bypasses the EO stripper and therefore reduces the stripping steam that is required by the EO stripper.

In another preferred embodiment, an additional 5-60%, more preferably 7-40%, and most typically 10-25% of the dilute ethylene oxide solution obtained from the EO absorber bypasses both the EO stripper and the EO reabsorber and is mixed with surplus EO reabsorber bottoms and the acetaldehyde-EO purge stream from the HPEO Column and passed directly to a second lights stripper for use as feed to the glycol reactor, and never passes through the EO stripper or the EO reabsorber, thus reducing the stripping steam consumed in the EO stripper by an additional 10-25%.

DETAILED DESCRIPTION

Figure 1:
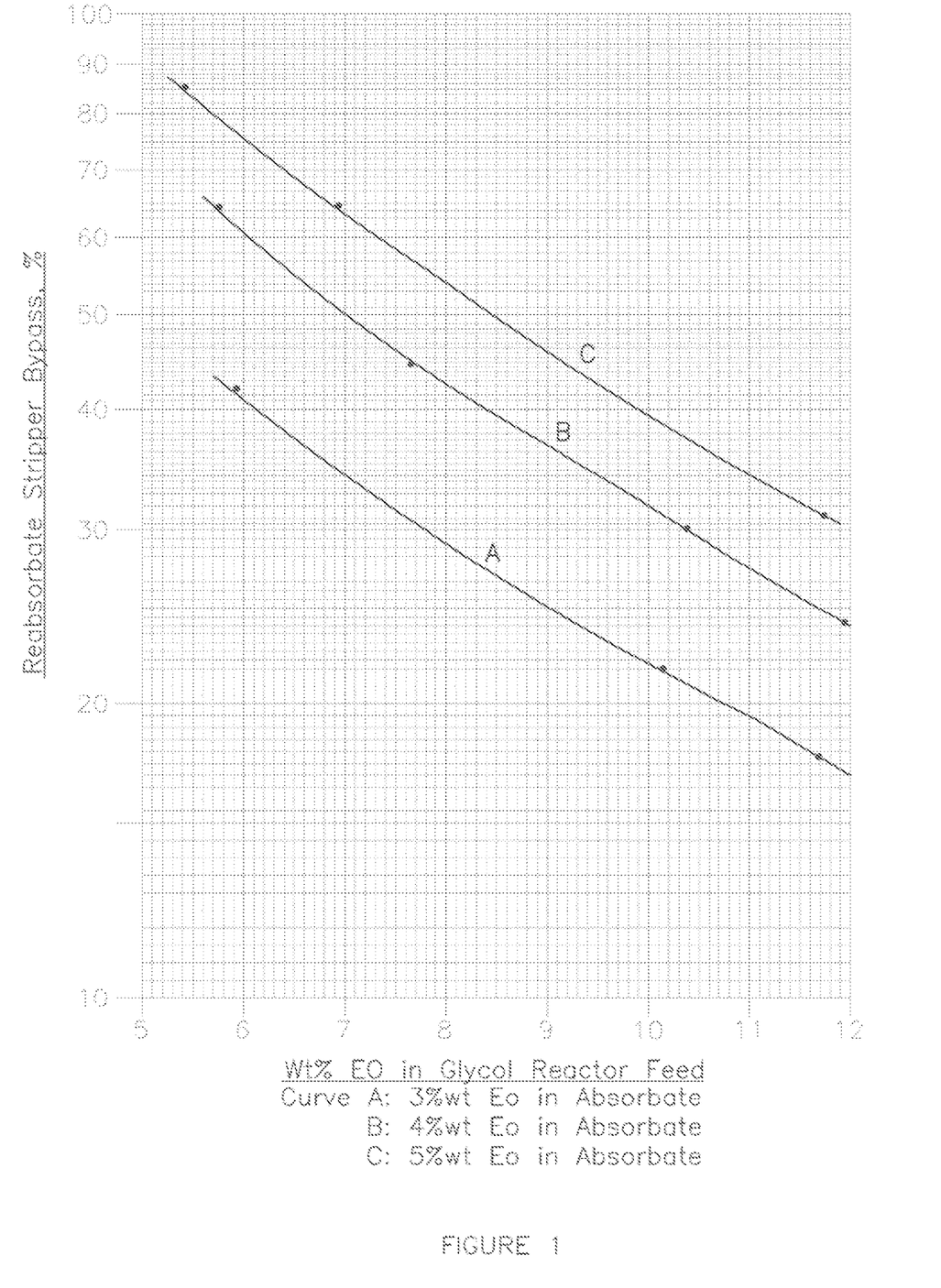
FIG. 1 shows how the maximum potential EO stripper bypass rates (and the related stripper steam savings) are related to the EO concentration in the EO reabsorber bottoms.

According to embodiments of the invention, incorporation of an additional lights stripper into a combined ethylene oxide/ethylene glycol plant that utilizes a stream that bypasses the ethylene oxide stripper column permits a greater percentage of the ethylene oxide to not only bypass the ethylene oxide stripper column, but also to bypass the ethylene oxide reabsorber column. FIG. 1 shows how the maximum potential EO Stripper Bypass rates (and the related stripper steam savings) are related to the EO concentration in the EO Reabsorber bottoms. This plot demonstrates the energy savings that may be realized by the production scheme in FIG. 3 as compared to the scheme in FIG. 2. This is because a portion of the EO absorbate from the initial EO absorber column 1300 can bypass both the EO stripper 1311 and the EO reabsorber 1327 in the FIG. 3 scheme. In the FIG. 2 scheme, a portion of the EO absorbate from the initial EO absorber column 300 can bypass only the EO stripper 311. Therefore in the inventive scheme, shown in FIG. 3, the total amount of EO absorbate that can be bypassed is 40-60 weight % of the process stream compared to 20-30% weight percent in the FIG. 2 scheme.

Figure 2:
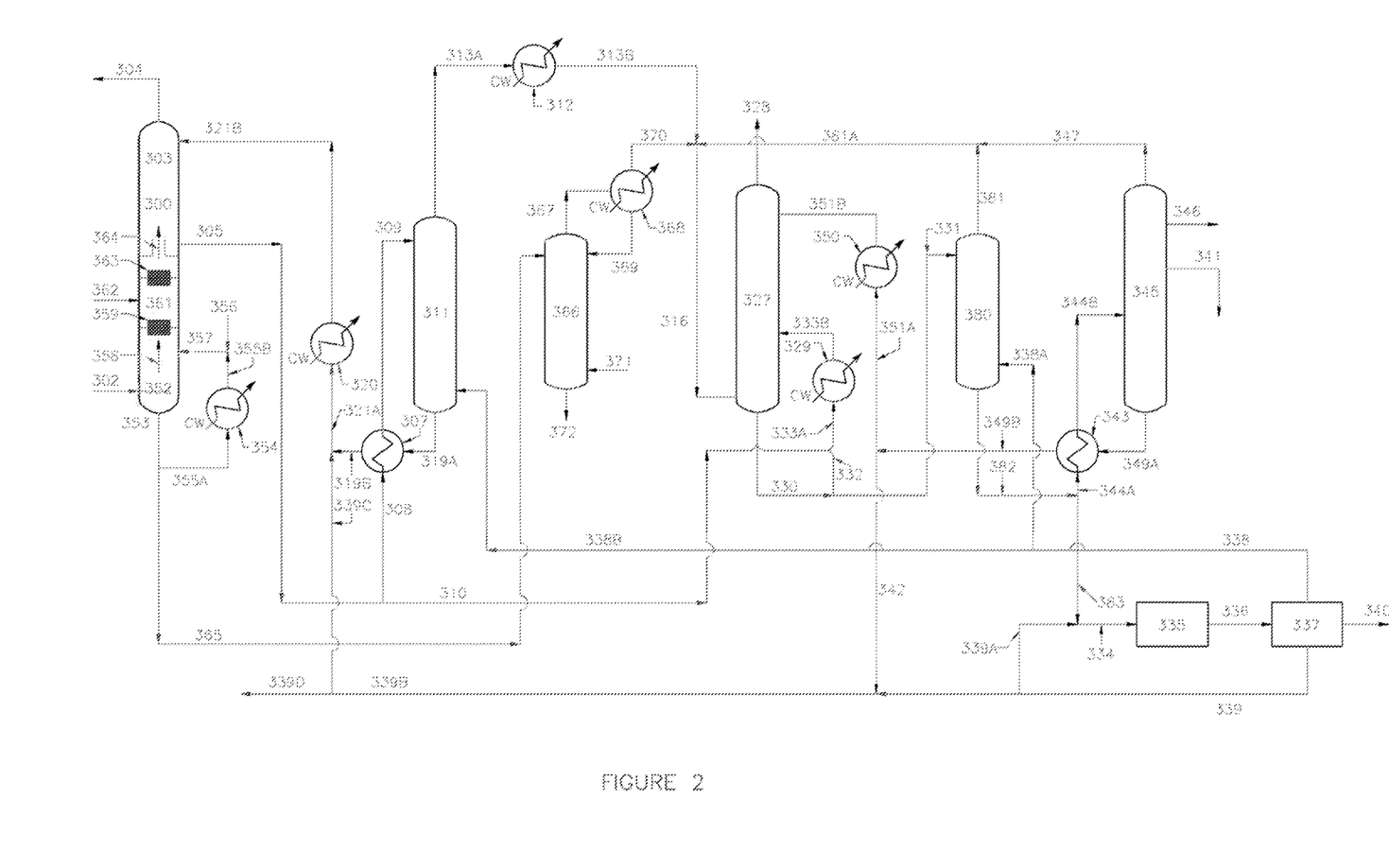
FIG. 2 is a schematic representation of a flow scheme for an EO reaction system that includes an EO Stripper Bypass stream and a single Lights Stripper that produces the EO feeds for both the EO Purification Column and the MEG reactor.

An exemplary ethylene oxide recovery process as described in U.S. Pat. No. 7,569,710 that has an ethylene oxide bypass stream is shown in FIG. 2. This process will be described in detail, since the inventive process comprises certain elements of this process.

Generally, the process as shown in FIG. 2 depicts a process of purifying and concentrating the effluent from a catalytic reactor that oxidizes ethylene gas to ethylene oxide, but includes an ethylene oxide bypass stream, i.e. a stream that bypasses the main EO stripping column. As is known in the art, impurities in the reaction effluent that are byproducts of the oxidation reaction and other side reactions may include water, carbon dioxide, various aldehydes, e.g. formaldehyde and acetaldehyde, as well as organic acids, among others. These need to be removed and in addition, the purified ethylene oxide needs to be provided in the correct concentrations in order to be suitable for further purification steps, and/or to be fed to a reactor that produces high grade ethylene glycol, or mono ethylene glycol (also referred to as EG or MEG) that is suitable to be used in the production of fiber-grade polyester. Utilizing the process described below allows some of the ethylene oxide stream from an ethylene oxide absorber to bypass an ethylene oxide stripper column, be diluted with clean process water and go directly to a glycol reactor.

Referring to FIG. 2, effluent gas containing ethylene oxide from an EO reaction system (not shown) is introduced directly into the bottom section of a quench scrub section 352 of a column 300 via conduit 302. Note that in this embodiment, the quench (or quench scrub) section 352 comprises the bottom of the column 300, but in alternative embodiments, the quench scrubbing step could be performed in a separate dedicated column. Quench bottoms solution is recirculated via conduits 353 and 355A, through cooler 354, and conduits 355B and 357 to the top of the quench scrubbing section 352 of the column 300. This is clear in FIG. 2 where conduit 357 is shown entering the absorber column 300 at a point above the bottom, but well below the top of column 300.

An alkaline solution, in the form of concentrated sodium hydroxide (for instance, 10-20 wt. % as an aqueous solution) is injected into the recirculated quench solution via conduit 356. The NaOH neutralizes dissolved $CO_2$ which is present as a contaminant and thus converts into sodium carbonate and sodium bicarbonate. The basic solution also neutralizes organic acids, which are likewise are present as contaminants from the oxidation reaction. A cooled, scrubbed vapor, which is free of organic acid vapor, but contains some formaldehyde and entrained quench liquid, thus emerges from the top of the quench section 352 and is passed through a demister unit 359 to remove the entrained liquid. This cooled, scrubbed vapor then enters an upper water wash section 361 above the quench section 352 of the column 300.

The filtered quench gas is then washed in water wash section 361 with fresh purified water, that is introduced via conduit 362. This water removes any remaining entrained quench liquid and absorbs most of the remaining formaldehyde and water-soluble heavy impurities. A countercurrent water wash will preferably be used for this step. This countercurrent water wash step may optionally be preceded by a recirculated water wash section for maximum vapor-liquid contact. The net wash water from the bottom of the water wash section(s) may drain into the top of the lower quench section 352. This water thus dilutes the concentration of formaldehyde and other undesirable impurities in the quench liquid and accordingly reduces the equilibrium concentration of these impurities in the scrubbed gas feed to the EO absorber section 303 located in the upper section of column 300. The net quench bottoms solution bleed stream, containing condensed water, wash water, absorbed impurities and some ethylene oxide, flows via conduits 353 and 365 to a quench bleed stripper 366.

The quenched/scrubbed washed gas from the top of the water wash section, is passed through a second demister unit 363 to remove any entrained wash water from conduit 362. This gas enters the EO absorber section 303. Cold EO-free absorption water is introduced into the upper section of absorber section 303 via conduit 321B. The quenched/scrubbed washed gas (i.e. reaction effluent gas after passing through sections 352 and 361 of column 300) is countercurrently contacted by the cold absorbent water to absorb almost all of the ethylene oxide entering the absorber section 303 of column 300. The non-condensable, non-absorbable-in-water gas remaining from the reaction effluent gas leaving the top of absorber 303 is essentially free of ethylene oxide and is returned to the EO reaction system via conduit 304. The dilute EO-water solution (i.e. the EO as absorbate) that is formed in absorber 303 is withdrawn from the bottom of the absorption section via conduit 305.

In the flow scheme shown in FIG. 2, part of the EO absorbate in conduit 305 bypasses EO stripper 311 and flows directly to an EO reabsorber bottoms recycle cooler 329 via conduits 310 and 333A. The amount bypassed will vary between 25-35 weight % of the total absorbate solution exiting at conduit 305. The amount of absorbate solution that bypasses the EO stripper 311 depends on the EO concentration in the absorbate solution and depends on the desired EO concentration in the reabsorber bottoms (and feed to an EO purification unit or a glycol reactor). The amount bypassed can be determined using tables, equations, or graphs.

The balance of the absorbate solution (i.e., the portion that was not bypassed and sent to the cooler 329) is introduced into an EO stripper preheater exchanger 307 via conduit 308, and the hot rich absorbate solution, from preheater exchanger 307 is fed to an upper portion of EO stripper 311, via conduit 309. Stripping steam, which may be extracted from a downstream glycol plant, is introduced to a lower portion of stripper 311 via conduit 338B or the stripping steam may be generated internally by a reboiler (not shown). By countercurrent contact of the absorbate solution and steam within stripper 311, the absorbate solution is stripped of the ethylene oxide, which together with steam, carbon dioxide, light ends, and trace impurities is withdrawn from the top of stripper 311 via conduit 313A. The stripped (lean) absorbate solution, now comprising water essentially free of ethylene oxide, is withdrawn from the bottom of stripper 311 via conduit 319A and cooled in heat exchanger 307, giving up heat to the rich absorbate solution feed. The cooled lean absorbate solution from cooler 307 is passed via conduit 319B, combined with recycled water from the glycol plant and/or the EO purification tower 345 in conduit 321A to heat exchanger 320, where it is further cooled and the total lean (in EO) absorbate solution stream is recycled back to the top of absorber section 303 in column 300 via conduit 321B.

The rich absorbate solution fed to the EO stripper 311 in conduit 309 may contain from about 1 to about 5 wt. % of ethylene oxide and the stripper 311 is operated to recover more than 95% and usually more than 99% of the ethylene oxide contained in the rich absorbate solution fed to the stripper 311. Although the stripper 311 normally operates at close to atmospheric pressure, the temperatures in the stripper column 311 are high enough to cause about 0.5-3.0% of the total amount of EO in the solution of feed to thermally hydrate (i.e. react with the water) to form mainly monoethylene glycol. The glycol produced in the EO stripper will build up to a low, equilibrium concentration in the EO absorber and EO stripper recycle water system that is controlled by the amount of the absorbate solution that bypasses (via stream 310) the stripper, since this bypass stream effectively acts as a very large cycle water glycol bleed.

The overhead vapor withdrawn via conduit 313A from the EO stripper 311, usually contains about 20 to 30 mole % of ethylene oxide. The primary diluent in this vapor stream is water, although about 7-10 mole % is generally non-condensable gases. These non-condensable gases predominantly comprise $CO_2$, but also may include nitrogen, argon, oxygen, methane, ethylene and ethane. The overhead vapor stream in conduit 313A from stripper 311 is cooled in heat exchanger 312. The heat exchanger 312 will condense some of the water in the overhead vapor emerging from the stripper 311 and then a total effluent mixture of the uncondensed EO-rich portion of the vapor and the condensate flows from the heat exchanger 312 via conduits 313B and 316 to an EO reabsorber 327.

The net quench bleed bottoms stream in conduit 353 from the quench scrubber portion 352 of column 300 comprises mainly excess water produced as a byproduct of the EO reaction that is partially condensed in the quench scrubber portion 352 plus makeup wash water. The quench bleed bottoms also comprises alkaline salts and absorbed ethylene oxide. This stream is sent, via conduit 365, to the small purge stripper 366 where the absorbed ethylene oxide is stripped out, using stripping steam that is injected into purge stripper 366 via conduit 371. The stripping steam for purge stripper 366 may alternatively be generated in a reboiler (not shown). A heat exchanger may be also used to preheat the stream fed to the purge stripper 366 in order to reduce the reboiler heat duty and/or to reduce the amount of stripping steam needed.

The overhead vapors emerging from the top of purge stripper 366 via conduit 367 are cooled in heat exchanger (or condenser) 368 to a temperature that is low enough such that a substantial part, preferably at least 60%, of the water contained in the overhead vapor from the purge stripper 366 is condensed. This condensate phase from heat exchanger/condenser 368 is contaminated with dissolved salts and formaldehyde and is drained or pumped back into the upper portion of the purge stripper 366 via conduit 369.

The remaining uncondensed portion of the cooled purge stripper overhead vapor is withdrawn from the heat exchanger/condenser 368 via conduit 370. As can be seen in FIG. 2, this uncondensed portion of the cooled purge stripper overhead vapor in conduit 370 is then combined with the EO and condensate mixture that emerges via conduit 313B from the heat exchanger 312 on the overhead from the main EO stripper 311. The stream in conduit 381, which is an overhead vapor stream emerging from a lights stripper 380, is also combined (via conduit 381A) with the streams in conduits 370 and 313B and a formaldehyde-rich stream in conduit 347 (also via conduit 381A) that emerges from the top of an EO purification unit 345. These four combined streams (conduits 370, 313B, 381 and 347) are introduced, via conduit 316, into a lower portion of the reabsorber 327. The EO-free aqueous bottoms from purge stripper 366, which contains most of the formaldehyde, salts, and a small amount of ethylene glycol are sent to waste treatment or technical grade glycol recovery via conduit 372.

Some recycled cold water is introduced to an upper portion of the reabsorber 327 via conduit 351B. Within the upper portion of the reabsorber 327, the combined light gases in conduit 316 from the overhead vapor streams from the EO stripper 311, the quench purge stripper 366, the lights stripper 380 and the EO purification column 345 and the cold water from conduit 351B are counter-currently contacted to absorb the maximum amount possible of the ethylene oxide contained in the combined vapor streams of conduit 316. The non-condensed gases emerging from the top of reabsorber 327, that normally contain only trace amounts of ethylene oxide are vented via conduit 328. Since this vent stream in conduit 328 contains a significant amount of hydrocarbons, comprising mainly ethylene and methane, it is preferably compressed and recycled back to the EO reactor gas system for (partial) recovery of the contained ethylene. In some plants, particularly those that have a small production capacity, the reabsorber vent gas in conduit 328 may be vented to the atmosphere, or preferably incinerated to avoid atmospheric pollution.

The EO-rich reabsorbate is withdrawn from the bottom of reabsorber 327 via conduit 330. This reabsorbate is pressurized using a pump (not depicted) and divided into two portions shown as conduits 331 and 332. A portion that is the net bottoms product (i.e., second portion of the bottoms are cooled and recycled back to the EO reabsorber 327) flows through conduit 331 to the top of the lights stripper 380. The aqueous reabsorbate bottoms comprises not only the reabsorbed ethylene oxide vapor but also comprises acetaldehyde and dissolved carbon dioxide as well as dissolved non-condensable gases. The mass balance of water in the absorber-stripper system may be maintained by injecting low pressure process steam extracted from the glycol plant directly into the EO stripper 311 to provide up to 100% of the stripping vapor required and/or by recycling water from the glycol plant evaporation section for use as absorption water.

As described in U.S. Pat. No. 4,134,797, the portion of the EO-rich reabsorbate withdrawn via conduit 330 that goes into conduit 331 will first pass into the lights stripper column 380 (also referred to as the carbon dioxide stripping column). In the lights stripper column 380 the liquid in conduit 331 is stripped of $CO_2$ and light gases, such as ethane and ethylene. Stripping steam is supplied to the bottom of the lights stripper column 380 from an evaporation train 337 via conduits 338 and 338A. The $CO_2$-rich EO vapor that exits lights stripper 380 via conduit 381 is combined with the overhead vapor purge from the EO purification column 345 in conduit 381A, is mixed with the main EO feed vapor stream in conduit 316 and then enters the bottom of reabsorber 327, as described above. The essentially gas-free bottoms, (purified aqueous solution of EO) from the carbon dioxide (lights) stripping column 380 are then pumped to a glycol reaction unit 335 via conduits 382, 383, and 334 and to the EO purification unit via conduits 382, 344A and 344B. Note however, that in this process, this bottoms stream in conduit 383 is too concentrated in EO for the ethylene glycol reactor 335 and that therefore it is diluted with process recycle water provided via conduit 339A that originates from the evaporation train 337 to provide the final feed in conduit 334 to the glycol reactor 335.

In the reabsorber unit 327, the recycled reabsorbate flowing through conduit 332 is combined with bypassed rich absorbate in conduit 333A, cooled in heat exchanger 329 and introduced as cold liquid to a middle portion of reabsorber 327 via conduit 333B. Heat exchanger 329 maintains the reabsorber in heat balance to achieve the pre-determined bottom reabsorbate temperature and hence the desired concentration of ethylene oxide. Depending on the operating pressure of the reabsorber 327 and the amount of bypassed dilute absorbate in conduit 310, the ratio of reabsorbate recycled via conduit 332 to the net reabsorbate withdrawn via conduit 331 will range from as low as no recycle to as high as a ratio of 3:1. The maximum bypass of EO-rich absorbate (not shown) may be achieved when the bypassed absorbate in stream 310 is separately cooled and introduced into reabsorber 327 at a point above the recycled bottom reabsorbate.

The reabsorbate in conduit 344A (from the bottoms of stripper 380 via conduit 382) flowing to EO purification is preheated in heat exchanger 343 and fed to the lower part of the single EO purification column 345 via conduit 344B, where it is separated into a purified side-stream EO liquid product (stream 346), and a small formaldehyde-rich crude EO overhead vapor purge stream (stream 347) that is recycled back to the reabsorber 327 for recovery of the EO, as described above. In addition, an impure side stream of acetaldehyde-rich EO is removed from the EO purification column 345 via conduit 341 to purge the acetaldehyde. Although not shown, this stream is mixed with the stream in conduit 334 and sent to the glycol reaction unit 335. The EO-free bottoms water stream containing most of the trace amount of formaldehyde that was in the feed to the EO purification column 345, is withdrawn via conduit 349A, cooled in heat exchanger 343 and a portion is recycled to the reabsorber 327 via conduits 349B, 351A, and 351B. The EO free bottoms not required in the reabsorber 327 are recycled via conduit 342 and combined with recycle condensate from the evaporation train 337 in conduit 339B.

In the glycol reactor 335, the ethylene oxide in the degasified lights stripper bottoms feed that has been mixed with recycle evaporator condensate via conduit 339A to increase the water-to-EO ratio (as required to reduce the formation of heavy glycols) and the small acetaldehyde-EO purge in conduit 341 from the EO purification unit 345 is almost completely reacted with water to form mixed ethylene glycols. The effluent from the glycol reactor 335 is fed to the multiple-effect evaporation train 337 in which the water is separated from the concentrated crude glycol that is then fed to glycol purification (not shown) via conduit 340. Part of the water separated in evaporation train 337 is recycled back to the EO plant as steam via conduit 338 and injected directly into the lights stripper 380 (via conduit 338A) and EO stripper 311 (via conduit 338B) to provide up to 100% of the required stripping steam. The balance of the recovered evaporation water is recycled back to the EO plant via conduit 339 and is combined with the balance of the bottoms from EO purification column 345 in conduit 339B. To provide the required flow of absorption water to the EO absorber 303, makeup recycle water is added via conduits 339B, 339C, 321A and 321B and surplus recycle water is sent to a recycle surge tank (not shown) via conduit 339D.

An embodiment of the present invention as applied to plants that produce both EO and mono-ethylene glycol as described above is shown in FIG. 3.

Figure 3:
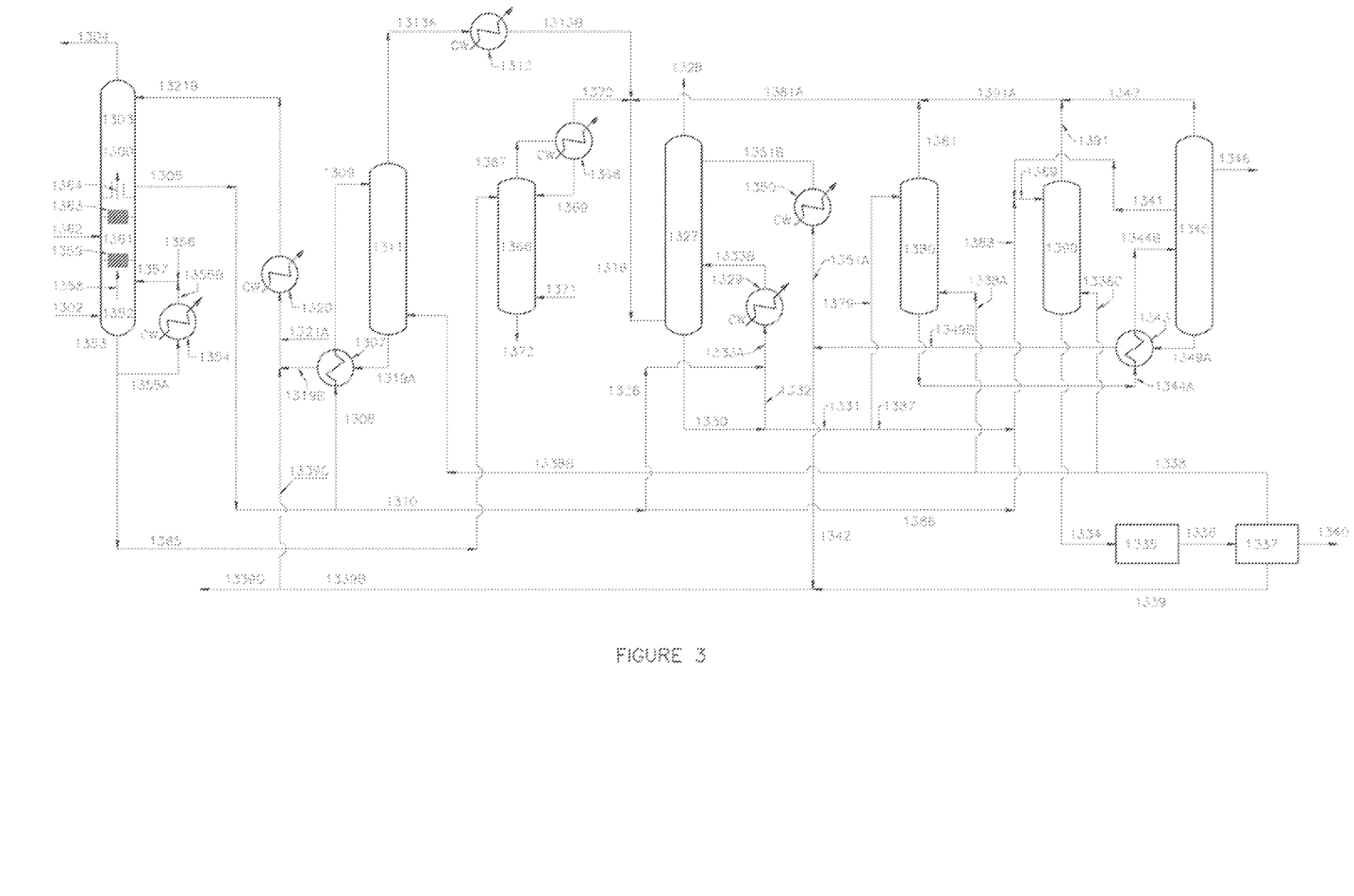
FIG. 3 is a schematic representation of an exemplary embodiment of the invention showing a flow scheme which is the process as shown in FIG. 2 with the addition of a second Lights Stripper.

Referring to FIG. 3, effluent gas from the EO reaction system (not shown) containing ethylene oxide (EO) is introduced directly into a bottom of quench/scrubbing section 1352 of column 1300 via conduit 1302. Quench bottoms solution is recirculated via conduits 1353 and 1355A, cooler 1354, and conduits 1355B and 1357 to the top of the quench scrubbing section 1352. Concentrated sodium hydroxide (10-20 wt. % aqueous solution) is injected into the recirculated quench solution via conduit 1356 to react with dissolved $CO_2$ and be converted into sodium carbonate and bicarbonate, which then neutralize byproduct organic acids. The cooled, scrubbed vapor from the top of the quench section 1352, which is free of organic acid vapor, but contains some formaldehyde and entrained quench liquid is passed through a demister unit 1359 to remove the entrained liquid and then enters the upper wash section 1361 above the quench section 1352 of the column 1300.

The filtered quench gas is then washed with fresh purified water, introduced via conduit 1362, to completely remove any remaining entrained quench liquid and to absorb most of the remaining formaldehyde and heavy impurities. A countercurrent water wash will preferably be used, which can be preceded by a recirculated water wash section for maximum vapor-liquid contact. The net wash water from the bottom of the water wash section(s) in column 1300 may drain into the top of the lower quench section 1352, diluting the concentration of formaldehyde and other undesirable impurities in the quench liquid and reducing the equilibrium concentration of these impurities in the scrubbed gas feed to the upper part of column 1300. The upper part of column 1300 is an EO absorber section 1303. The net quench bottoms solution bleed, containing condensed water, wash water, absorbed impurities and some ethylene oxide, flows via conduits 1353 and 1365 to a quench bleed stripper 1366.

The washed vapor from the water wash section 1361, is passed through a demister unit 1363 in column 1300 to remove any entrained wash water and enters the EO absorber section 1303 of column 1300. Cold EO-free absorption water is introduced into the upper section of absorber section 1303 via conduit 1321B and the reaction effluent gas is counter currently contacted by the water to absorb almost all of the ethylene oxide entering the absorber. Note that this water in conduit 1321B may be recycled from an evaporation train 1337 which follows a glycol reactor 1335. The non-condensable reaction gas, comprising inter alia, unreacted ethylene, leaving the top of absorber section 1303 is essentially free of ethylene oxide and is returned to the EO reaction system via conduit 1304. The dilute EO-water solution (i.e. the EO absorbate) that is formed in absorber section 1303 is withdrawn from the bottom of the absorption section 1303 via conduit 1305.

Optionally, the three sections of column 1300 may be comprised of two or three separate columns.

Part of the EO absorbate in conduit 1305 bypasses EO stripper 1311 and flows directly to the EO reabsorber bottoms recycle cooler 1329 via conduits 1310, 1326 and 1333A. The amount of EO absorbate in conduit 1305 that bypasses the EO stripper 1311 may vary between 15-75%. The amount of EO absorbate in conduit 1305 that can bypass the EO stripper 1311 depends on the EO concentration in the EO absorbate and the desired EO concentration in the reabsorber 1327 bottoms in conduit 1330 (and glycol reactor feed), and can be determined using tables, equations, or graphs.

In this inventive flow scheme, a significant additional part of the EO absorbate that exits the bottom of column 1300 will bypass both the EO stripper 1311 and the EO reabsorber 1327 and a first lights stripper 1380 via conduit 1386 and go directly to a second lights stripper 1390. As can be seen in FIG. 3, this EO absorbate that has bypassed the EO stripper 1311, the EO reabsorber 1327 and a first lights stripper 1380 via conduit 1386 is used instead of recycled process water to dilute a portion of the more concentrated bottoms from EO reabsorber 1327 provided by conduit 1387 in conduit 1388. By controlling the flow of bypassed absorbate in conduit 1386, the diluted EO absorbate that ultimately emerges as the bottoms from the second lights stripper 1390 has the desired lower EO concentration that may be fed directly to the glycol reactor 1335. The addition of the second lights stripper 1390 to degasify only the feed to the MEG reactor 1335 is therefore a significant process improvement from the flow scheme as shown in FIG. 2 and significantly increases the amount of EO absorbate that can bypass the EO stripper 1311. This additional amount of process stream that bypasses the EO stripper 1311 means that less heat and electrical energy is needed to operate the EO stripper 1311 and the EO reabsorber 1327 compared to a process that does not utilize the second lights stripper 1390 (also referred to as the MEG lights stripper). Notably, the total energy load on both strippers 1380 and 1390 is approximately the same as the total of the single stripper 380 in FIG. 2.

The balance of the EO absorbate that exits the column 1300, i.e., the portion of the EO absorbate stream from conduit 1305 that does NOT bypass the EO stripper 1311 and the EO reabsorber 1327, is introduced into an EO stripper preheater exchanger 1307 via conduit 1308, and the hot EO absorbate from preheater 1307 is fed to an upper portion of the EO stripper 1311, via conduit 1309. Low pressure stripping steam extracted from a downstream glycol plant 1335 is introduced to a lower portion of EO stripper 1311 via conduit 1338B. The stripping steam may optionally be generated internally by a reboiler (not shown). The water balance in the absorber-stripper system may be maintained by directly injecting low pressure process steam extracted from the glycol plant 1335 directly into the EO stripper 1311 to provide up to 100% of the stripping vapor required and/or by recycling water from the glycol plant evaporation section 1337 for use as absorption water.

By countercurrent contact of the EO absorbate and steam within the EO stripper 1311, the EO absorbate is stripped of the ethylene oxide, which together with steam, carbon dioxide, light ends and trace impurities is withdrawn from the top of the EO stripper 1311 via conduit 1313A. The stripped absorbate, now essentially free of ethylene oxide and thus comprising mostly water with a small concentration of ethylene glycol, is withdrawn from the bottom of the EO stripper 1311 via conduit 1319A and cooled in heat exchanger 1307, giving up heat to the rich absorbate feed. The cooled lean aqueous absorbate from the heat exchanger 1307 is passed via conduit 1319B, combined with recycled water from the evaporation train 1337 of the glycol plant and the EO purification tower 1345 via conduit 1339C, and finally, in conduit 1321A is passed to heat exchanger 1320, where it is further cooled and the total lean aqueous absorbate stream is recycled back to top of absorber section 1303 via conduit 1321B.

The rich (in EO) absorbate feed in conduit 1309 to the EO stripper 1311 may contain from about 1 to about 5 wt. % of ethylene oxide and the EO stripper 1311 is operated to recover more than 95% and usually more than 99% of the ethylene oxide contained in the feed. Although the EO stripper 1311 normally operates at close to atmospheric pressure, the temperatures in the EO stripper column 1311 are high enough to thermally hydrate in the range of 0.5-3.0% of the EO feed to ethylene glycol. The glycol thus produced in the EO stripper 1311 will build up to a low, equilibrium concentration in the EO absorber—EO stripper recycle water system that is controlled by the amount of the absorbate that bypasses the EO stripper 1311 via stream 1310, which acts as a very large cycle water/glycol bleed.

The overhead vapor withdrawn from the EO stripper 1311 via conduit 1313A usually contains about 20 to 30 mole % of ethylene oxide. The primary diluent in this vapor stream is water, although about 7 to 10 mole % can be generally referred to as non-condensable gases, and is predominantly $CO_2$, but also includes nitrogen, argon, oxygen, methane, ethylene and ethane. The EO stripper 1311 overhead vapors are cooled in heat exchanger 1312 and the total effluent mixture of uncondensed vapor and condensate flows via conduits 1313B and 1316 to the EO reabsorber 1327.

The net bleed bottoms stream from the quench section 1352 of column 1300 comprises mainly the water formed as a byproduct of the oxidation of ethylene to EO that is partially condensed in the quench scrubber section 1361/1352 plus makeup wash water from section 1361 and also contains some alkaline salts and absorbed ethylene oxide. This stream is sent, via conduit 1365, to a small purge stripper 1366 where the absorbed ethylene oxide is stripped out, using stripping steam injected via conduit 1371, or generated in a reboiler (not shown). A purge stripper feed/bottoms heat exchanger may be also used to reduce the reboiler heat duty and/or the amount of stripping steam. The overhead vapors from purge stripper 1366 are cooled in a heat exchanger 1368 to a temperature such that a substantial part, preferably at least 60%, of the contained water is condensed. The contaminated condensate phase from the condenser 1368 is drained or pumped back into the upper portion of the purge stripper 1366 via conduit 1369. The uncondensed overhead vapor from purge stripper 1366 is withdrawn from the condenser 1368 via conduit 1370, combined with the EO and condensate mixture from condenser 1312 and the recycled EO vapor in conduit plus the contents of conduit 1381A and introduced into a lower portion of the EO Reabsorber 1327 via conduit 1316. Conduit 1381A contains the combined vented vapors from the first lights stripper 1380 (which produces feed to the high purity ethylene oxide (HPEO) column 1345), the second lights stripper 1390 (which produces the feed to the monoethylene glycol plant 1335) and the HPEO column 1345 in conduit 1316 and introduced into a lower portion of the EO reabsorber 1327. The EO-free aqueous bottoms from the purge stripper 1366, containing most of the formaldehyde, salts, and a small amount of ethylene glycol are sent to waste treatment or technical grade glycol recovery via conduit 1372.

Some recycle cold water is introduced to an upper portion of the EO reabsorber 1327 via conduit 1351B. Within the upper portion of the EO reabsorber 1327, the light gases in the overhead vapor from EO stripper 1311 and the water from conduit 1351B are counter-currently contacted in order to absorb the maximum amount possible of the ethylene oxide contained in the vapor into the water. The non-condensable gases emerging from the top of the EO reabsorber 1327, normally containing only trace amounts of ethylene oxide are vented via conduit 1328. Since this vent stream in conduit 1328 contains a significant amount of hydrocarbons, comprising mainly ethylene and methane, it is preferably compressed and recycled back to the EO reactor gas system for maximum recovery of the contained ethylene. In some plants, particularly those of small production capacity, the reabsorber vent gas may be vented to atmosphere, or may be incinerated to avoid atmospheric pollution.

The EO-rich reabsorbate is withdrawn from the bottom of the EO reabsorber 1327 via conduit 1330. This reabsorbate in conduit 1330 is pressurized using a pump (not depicted) and divided into three portions. The first portion of reabsorbate from EO reabsorber 1327 is recycled via conduit 1332, mixed with EO bypass from conduit 1326 in conduit 1333A, cooled in heat exchanger 1329 and fed to the middle of the EO reabsorber column 1327.

The second portion of reabsorbate from EO reabsorber 1327 is the largest portion of the net bottoms product and flows through conduits 1331 and 1379 to the top of the first lights stripper 1380 (also referred to as the HPEO lights stripper 1380).

The third portion of reabsorbate from the EO reabsorber 1327 is the balance of the net bottoms product and flows through conduits 1331, 1387, 1388 and 1389 to the top of the second lights stripper 1390, also referred to as the MEG lights stripper 1390. Notably, the aqueous reabsorbate from EO reabsorber 1327 contains not only the reabsorbed ethylene oxide vapor from the EO stripper 1311, but also contains dissolved carbon dioxide and non-condensable gases that need to be removed before the stream can be fed to the glycol reactor, 1335. Degasifying the third portion of reabsorbate and the gasified diluent bypassed absorbate is the purpose of this second lights stripper 1390.

The flow rate of the EO-rich reabsorbate from the EO reabsorber 1327 to the HPEO (first) lights stripper 1380 is controlled to supply only the exact quantity of EO feed required by the HPEO Column 1345. In the first lights stripper 1380, the reabsorbate feed to the HPEO column 1345 is stripped of carbon dioxide and other light gases using stripping steam that is supplied to the bottom of the column 1345 from the evaporation train 1337 via conduits 1338 and 1338A. The gas-free bottoms from the first lights stripping column 1380 are then pumped and fed to the lower part of EO purification column 1345 via conduits 1344A and 1344B and preheater 1343.

In the high purity EO (HPEO) purification column 1345, the reabsorbate feed (conduit 1344B) is separated into a purified side-stream EO liquid product (stream 1346), a small formaldehyde-rich crude EO overhead vapor purge stream (stream 1347) that is recycled back to the EO reabsorber 1327 for recovery of the EO, and an impure side stream of acetaldehyde-rich EO that is removed via conduit 1341 and sent to the MEG (second) lights stripper 1390 to be fed to the glycol reaction unit 1335. An EO-free bottoms water stream containing most of the trace amount of formaldehyde in the purification column 1345 feed, is withdrawn from column 1345 via conduit 1349A, cooled in heat exchanger 1343 and a portion is recycled to the EO reabsorber 1327 via conduits 1349B, 1351A, and 1351B. The EO-free bottoms not required in the reabsorber 1327 is recycled via conduit 1342, to be combined with recycle condensate from the evaporation train 1337 in conduit 1339B.

The balance of the total EO-rich reabsorbate withdrawn from EO reabsorber 1327 via conduit 1331 that is not fed to HPEO (first) lights stripper 1380 is withdrawn via conduit 1387, mixed with the part of the total bypass absorbate that is withdrawn via conduit 1386 and after combining with the acetaldehyde-EO purge stream in conduit 1341 from a high purity EO column 1345, the entire mixture is fed to the top of MEG (second) lights stripper 1390 via conduit 1389. The concentration of the EO in the 1386 conduit is sufficiently low to dilute the feed mixture in conduit 1389 such that the bottoms product from the second lights stripper 1390 in conduit 1334 is the appropriate low EO concentration to be fed to the glycol reactor 1335. Importantly, the EO/water in the 1386 conduit has bypassed both the EO stripper 1311 and the EO reabsorber 1327.

Optionally, the lights-free acetaldehyde-EO purge stream in conduit 1341 (from high purity EO column 1345) can be injected into the bottom of the second lights stripper 1390 to minimize the amount of acetaldehyde that is contained in the overhead vapor from the second lights stripper 1390.

Stripping steam is supplied from the evaporation train 1337 via conduits 1338 and 1338C to the bottom of the MEG (second) lights stripper 1390. The light gases that are stripped out exit the second lights stripper 1390 via conduit 1391 and are combined with formaldehyde-rich gas from the EO purification column 1345 in conduits 1391A, $CO_2$ rich product from the HPEO (first) lights stripper 1380 in conduit 1381A and then combined with vapor/liquid effluent from the cooler 1312 and the top vapor product of the small purge stripper 1366 in conduit 1316, entering the bottom of the EO reabsorber 1327. The gas-free bottoms product containing EO and water from the MEG (second) lights stripper 1390 is then pumped to the glycol reaction unit 1335 via conduit 1334, as noted above.

In the glycol reactor 1335, the ethylene oxide in the degasified second lights stripper 1390 bottoms is almost completely reacted with water to form ethylene glycols. The effluent from the glycol reactor 1335 is fed to the multiple-effect evaporation train 1337 in which the water is separated from the concentrated crude glycol that is then fed to a glycol purification process (not shown) via conduit 1340. Part of the water separated in the evaporation train 1337 is recycled back to the various unit operations (as described above) of the EO plant as steam via conduits 1338 and injected directly into the HPEO (first) lights stripper 1380 (via conduit 1338A), MEG (second) lights stripper 1390 (via conduit 1338C) and the EO stripper 1311 (via conduit 1338B) to provide up to 100% of the required stripping steam. Steam from the evaporation train 1337 may also be utilized for the high purity ethylene oxide distillation column 1345.

The balance of the recovered evaporation condensate from the glycol evaporation train 1337 is recycled back to the EO plant via conduit 1339 and combined with the balance of the bottoms from the EO purification column 1345 in conduit 1339B. To provide the required flow of absorption water to the EO absorber section 1303, makeup recycle water is added via conduits 1339B, 1339C, 1321A and 1321B and surplus recycle water is sent to a recycle surge tank (not shown) via conduit 1339D.

Figure 4:
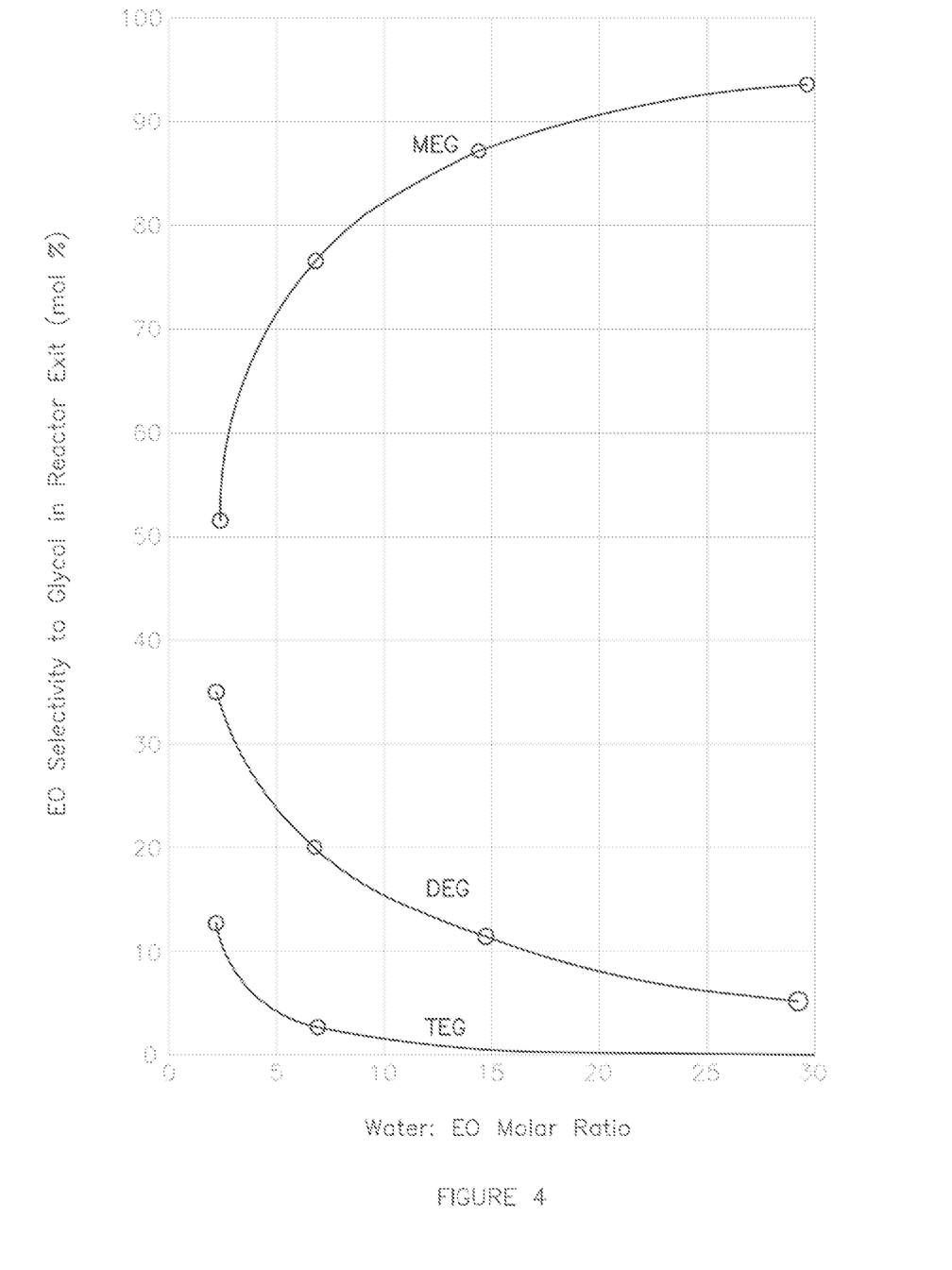
FIG. 4 is a graph showing the effect of increasing the water:EO ratio on the glycol reactor product distribution.

FIG. 4 is a graph showing the effect of increasing the water:EO ratio on the glycol reactor product distribution, demonstrating the necessity of having a more dilute ethylene oxide and water concentration to feed the glycol reactor 335 or 1335.

Non-limiting Aspects of the invention are as follows:

Aspect 1: A process for producing purified ethylene oxide (EO) and monoethylene glycol (MEG), the process comprising the steps of:

a) providing a quenched and alkaline treated and water washed vaporous reaction stream, wherein the quenched and alkaline treated and water washed vaporous reaction stream comprises EO, CO2, formaldehyde, and acetaldehyde;

b) contacting the quenched and alkaline treated and water washed vaporous reaction stream with water in an EO absorber to produce a first absorbate stream having a first EO concentration in water;

c) dividing the first absorbate stream into a first portion of the first absorbate stream, a second portion of the first absorbate stream, and a third portion of the first absorbate stream;

d) feeding the first portion of the first absorbate stream to an EO stripper and contacting the first portion of the first absorbate stream with steam to produce a vaporous EO stream;

e) feeding the vaporous EO stream to an EO reabsorber and contacting the vaporous EO stream with the second portion of the first absorbate stream to form a reabsorber bottoms stream, wherein the reabsorber bottoms stream has a second EO concentration in water that is higher than the first EO concentration in water;

f) dividing the reabsorber bottoms stream into a first portion of the reabsorber bottoms stream and a second portion of the reabsorber bottoms stream;

g) feeding the first portion of the reabsorber bottoms stream to a first lights stripper and contacting the first portion of the reabsorber bottoms stream with steam to produce a first lights stripper bottoms, wherein the first light stripper bottoms has a third EO concentration in water that is higher than the first EO concentration in water;

h) feeding the first lights stripper bottoms to a high purity ethylene oxide distillation column to produce purified EO;

i) combining the second portion of the reabsorber bottoms stream and the third portion of the first absorbate stream to produce a second lights stripper feed;

j) feeding the second lights stripper feed to a second lights stripper and contacting the second lights stripper feed with steam to produce a second lights stripper bottom stream, wherein the second lights bottom stream has a fourth EO concentration in water that is lower than the third EO concentration in water; and k) feeding the second lights bottom stream to a glycol reactor to produce MEG.

Aspect 2: The process according to Aspect 1, wherein the first portion of the first absorbate stream is 30 wt. % to 80 wt. % of the first absorbate stream, the second portion of the first absorbate stream is 15 wt. % to 50 wt. % of the first absorbate stream, and the third portion of the first absorbate stream is 5 wt. % to 40 wt. % of the first absorbate stream.

Aspect 3: The process according to any of Aspects 1 and 2, wherein the first portion of the first absorbate stream is 40 wt. % to 60 wt. % of the first absorbate stream, the second portion of the first absorbate stream is 25 wt. % to 35 wt. % of the first absorbate stream, and the third portion of the first absorbate stream is 10 wt. % to 25 wt. % of the first absorbate stream.

Aspect 4: The process according to any of Aspects 1-3, wherein the high purity ethylene oxide distillation column further produces a purge stream comprising ethylene oxide and acetaldehyde and wherein the purge stream comprising ethylene oxide and acetaldehyde is fed to the second lights stripper.

Aspect 5: The process according to any of Aspects 1-4, wherein the high purity ethylene oxide distillation column produces a vaporous overhead stream comprising EO and formaldehyde and the vaporous overhead stream comprising EO and formaldehyde is fed to the EO reabsorber with the vaporous EO stream.

Aspect 6: The process according to any of Aspects 1-5, wherein the first lights stripper produces a vaporous overhead stream that comprises $CO_2$ and the vaporous overhead stream that comprises $CO_2$ is fed to the EO reabsorber with the vaporous EO stream.

Aspect 7: The process according to any of Aspects 1-6, wherein an evaporation train after the glycol reactor provides steam to at least one of the EO stripper, the first lights stripper, the second lights stripper, and the high purity ethylene oxide distillation column.

Aspect 8: The process according to any of Aspects 1-7, wherein the water that is contacted with the quenched and alkaline treated and water washed vaporous reaction stream in the EO absorber comprises recycled process water.

Aspect 9: The process according to any of Aspects 1-8, wherein the high purity ethylene oxide distillation column further produces a purge stream comprising the acetaldehyde and EO, and wherein step i) further comprises combining the purge stream comprising the acetaldehyde and EO with the second lights stripper feed.

Aspect 10: An apparatus for producing purified ethylene oxide (EO) and monoethylene glycol (MEG) from a quenched and alkaline treated and water washed vaporous reaction stream, wherein the quenched and alkaline treated and water washed vaporous reaction stream comprises EO, CO2, formaldehyde, and acetaldehyde, the apparatus comprising:

a) an EO absorber configured and arranged to contact the quenched and alkaline treated and water washed vaporous reaction stream with water to produce a first absorbate stream having a first EO concentration in water;

b) a first series of conduits configured and arranged to divide the first absorbate stream into a first portion of the first absorbate stream, a second portion of the first absorbate stream, and a third portion of the first absorbate stream;

c) an EO stripper configured and arranged to contact the first portion of the first absorbate stream with steam to produce a vaporous EO stream;

d) an EO reabsorber configured and arranged to contact the vaporous EO stream with the second portion of the first absorbate stream to form a reabsorber bottoms stream, wherein the reabsorber bottoms stream has a second EO concentration in water that is higher than the first EO concentration in water;

e) a second series of conduits configured and arranged to divide the reabsorber bottoms stream into a first portion of the reabsorber bottoms stream and a second portion of the reabsorber bottoms stream;

f) a first lights stripper configured and arranged to contact the first portion of the reabsorber bottoms stream with steam to produce a first lights stripper bottoms, wherein the first light stripper bottoms has a third EO concentration in water that is higher than the first EO concentration in water;

g) a high purity ethylene oxide distillation column configured and arranged to produce purified EO from the first lights stripper bottoms;

h) a series of conduits configured and arranged to combine the second portion of the reabsorber bottoms stream and the third portion of the first absorbate stream to produce a second lights stripper feed;

i) a second lights stripper configured and arranged to contact the second lights stripper feed with steam to produce a second lights stripper bottom stream, wherein the second lights bottom stream has a fourth EO concentration in water that is lower than the third EO concentration in water; and j) a glycol reactor configured and arranged to produce MEG from the second lights bottom stream.

Aspect 11: The apparatus according to Aspect 10, further comprising an evaporation train after the glycol reactor, wherein the evaporation train is configured and arranged to provide steam to at least one of the EO stripper, the first lights stripper, the second lights stripper, and the high purity ethylene oxide distillation column.

Aspect 12: The apparatus according to any of Aspects 10 and 11, wherein the high purity ethylene oxide distillation column is further configured and arranged to produce a purge stream comprising the acetaldehyde and EO, and wherein h) is further configured and arranged to combine the purge stream comprising the acetaldehyde and EO with the second lights stripper feed.

EXAMPLE: (Prophetic)

An EO plant has an EO reactor with a capacity to produce 260,000 metric tons per year (T/yr.) of EO, equivalent to 31.25 metric tons per hour (T/hr.) as feed to both a monoethylene glycol (MEG) plant that can process 100% of the EO and to an EO purification system with a capacity of 150,000 metric tons per year (T/yr.) of high purity ethylene oxide (HPEO). The EO purification section includes an EO stripper bypass stream (as shown in FIG.2) and the EO stripper/reabsorber system is designed to produce 10 wt. % EO in water feed to the high purity ethylene oxide (HPEO) column and to the MEG reactor, which permits 25% of the EO absorbate to bypass the EO stripper and reduces the stripping steam flow to the EO Stripper by 25% or about 11 tons per hour (T/hr.).

During normal operation with 10 wt. % EO in water, the EO feed to the MEG reactor is only 42% of the design capacity of the MEG reactor system (the combination of the MEG reactor and the evaporation train after the reactor). Therefore the amount of process steam that can be provided to the EO recovery and purification sections from the evaporation train of the MEG reactor system is much lower than the amount of steam required by the EO recovery section alone. Accordingly, the optimum EO concentration in the feed to the MEG reactor will normally be much lower than 10 wt. % in water so as to increase the amount of stripping steam that can be extracted from the evaporation train of the MEG reactor system and to reduce the undesirable formation of diethylene glycol (DEG) and triethylene glycol (TEG) and raise the yield of the desired MEG. As shown in FIG. 2, the water that would be normally be used to dilute the EO feed to the MEG reactor would be recycled EO-free process water (mainly process condensate from the evaporator section of the glycol reactor system) and as a result, the final EO concentration of the MEG reactor feed cannot affect the amount of absorbate that bypasses the EO Stripper.

As shown in FIG. 3, by installing a second lights stripper that would be used to degasify only the final diluted EO feed to the MEG reactor, all the diluent water required for the MEG reactor feed can be provided from additional absorbate that will bypass both the EO stripper and the EO reabsorber. Detailed simulations of the EO plant show that by diluting the EO feed to the MEG reactor to the maximum water concentration that the evaporation section can handle, the EO concentration would be about 6.4 wt. % (equivalent to a water to {EO+MEG} molar ratio of 33:1). To provide the required diluent water, an additional 14% of the EO absorbate would bypass the EO stripper and the EO reabsorber, resulting in a total of 40% of the absorbate bypassing the EO stripper. This additional bypass provides a total reduction in stripping steam usage of 17 T/hr. (i.e., an additional 6 T/hr. of steam can be saved due to the enhanced EO bypass).

In both the standard and enhanced EO bypass cases, the justification for increasing the water to {EO+MEG} molar ratio from about 22:1 (with 10 wt. % EO) to about 33:1 would be an increase in the MEG yield to about 92.5 wt. % (from about 90 wt. %) as shown in FIG. 4. The higher water concentration would result in an increase in the high pressure and medium pressure steam usage in the MEG reaction preheat and evaporation trains that largely would be offset by the increased low pressure process steam that would be extracted from the evaporation train and used in the EO plant in both cases.

What is claimed is:

1. A process for producing purified ethylene oxide (EO) and monoethylene glycol (MEG), the process comprising the steps of:
   a) providing a quenched and alkaline treated and water washed vaporous reaction stream, wherein the quenched and alkaline treated and water washed vaporous reaction stream comprises EO, $CO_2$, formaldehyde, and acetaldehyde;
   b) contacting the quenched and alkaline treated and water washed vaporous reaction stream with water in an EO absorber to produce a first absorbate stream having a first EO concentration in water;
   c) dividing the first absorbate stream into a first portion of the first absorbate stream, a second portion of the first absorbate stream, and a third portion of the first absorbate stream;
   d) feeding the first portion of the first absorbate stream to an EO stripper and contacting the first portion of the first absorbate stream with steam to produce a vaporous EO stream;
   e) feeding the vaporous EO stream to an EO reabsorber and contacting the vaporous EO stream with the second portion of the first absorbate stream to form a reabsorber bottoms stream, wherein the reabsorber bottoms stream has a second EO concentration in water that is higher than the first EO concentration in water;
   f) dividing the reabsorber bottoms stream into a first portion of the reabsorber bottoms stream and a second portion of the reabsorber bottoms stream;
   g) feeding the first portion of the reabsorber bottoms stream to a first lights stripper and contacting the first portion of the reabsorber bottoms stream with steam to produce a first lights stripper bottoms, wherein the first light stripper bottoms has a third EO concentration in water that is higher than the first EO concentration in water;
   h) feeding the first lights stripper bottoms to a high purity ethylene oxide distillation column to produce purified EO;
   i) combining the second portion of the reabsorber bottoms stream and the third portion of the first absorbate stream to produce a second lights stripper feed;
   j) feeding the second lights stripper feed to a second lights stripper and contacting the second lights stripper feed with steam to produce a second lights stripper bottom stream, wherein the second lights bottom stream has a fourth EO concentration in water that is lower than the third EO concentration in water; and
   k) feeding the second lights bottom stream to a glycol reactor to produce MEG.

2. The process according to claim 1, wherein the first portion of the first absorbate stream is 30 wt. % to 80 wt. % of the first absorbate stream, the second portion of the first absorbate stream is 15 wt. % to 50 wt. % of the first absorbate stream, and the third portion of the first absorbate stream is 5 wt. % to 40 wt. % of the first absorbate stream.

3. The process according to claim 1, wherein the first portion of the first absorbate stream is 40 wt. % to 60 wt. % of the first absorbate stream, the second portion of the first absorbate stream is 25 wt. % to 35 wt. % of the first absorbate stream, and the third portion of the first absorbate stream is 10 wt. % to 25 wt. % of the first absorbate stream.

4. The process according to claim 1, wherein the high purity ethylene oxide distillation column further produces a purge stream comprising ethylene oxide and acetaldehyde and wherein the purge stream comprising ethylene oxide and acetaldehyde is fed to the second lights stripper.

5. The process according to claim 1, wherein the high purity ethylene oxide distillation column produces a vaporous overhead stream comprising EO and formaldehyde and the vaporous overhead stream comprising EO and formaldehyde is fed to the EO reabsorber with the vaporous EO stream.

6. The process according to claim 1, wherein the first lights stripper produces a vaporous overhead stream that comprises $CO_2$ and the vaporous overhead stream that comprises $CO_2$ is fed to the EO reabsorber with the vaporous EO stream.

7. The process according to claim 1, wherein an evaporation train after the glycol reactor provides steam to at least one of the EO stripper, the first lights stripper, the second lights stripper, and the high purity ethylene oxide distillation column.

8. The process according to claim 1, wherein the water that is contacted with the quenched and alkaline treated and water washed vaporous reaction stream in the EO absorber comprises recycled process water.

9. The process according to claim 1, wherein the high purity ethylene oxide distillation column further produces a purge stream comprising the acetaldehyde and EO, and wherein step i) further comprises combining the purge stream comprising the acetaldehyde and EO with the second lights stripper feed.

* * * * *